United States Patent [19]
Iles

[11] Patent Number: 5,551,828
[45] Date of Patent: Sep. 3, 1996

[54] CONTAINER MOVER AND METHOD OF MOVING A CONTAINER

[75] Inventor: Kenneth E. Iles, Los Altos, Calif.

[73] Assignee: Abbott Laboratories, Abbott Park, Ill.

[21] Appl. No.: 330,281

[22] Filed: Oct. 27, 1994

[51] Int. Cl.⁶ .................................................. G01N 35/02
[52] U.S. Cl. ............................ 414/757; 422/62; 422/65
[58] Field of Search .................................... 414/754, 757, 414/274, 744.3; 422/62, 63, 65

[56] References Cited

U.S. PATENT DOCUMENTS

| | | | |
|---|---|---|---|
| 3,541,751 | 11/1970 | Ouebe et al. | 414/757 |
| 4,534,465 | 8/1985 | Rothermel et al. | 422/104 |
| 4,753,563 | 6/1988 | Spillers | 414/757 |
| 4,847,474 | 7/1989 | Engel et al. | 235/462 |
| 4,849,176 | 7/1989 | Sakagami | 422/65 |
| 5,286,959 | 2/1994 | Demachi | 422/62 |
| 5,455,006 | 10/1995 | Aota et al. | 422/63 |

FOREIGN PATENT DOCUMENTS

| | | | |
|---|---|---|---|
| 0479622 | 4/1992 | European Pat. Off. | 35/04 |
| 0315757 | 5/1989 | Germany | 33/49 |
| 8300393 | 2/1983 | WIPO | 35/4 |

*Primary Examiner*—David A. Bucci
*Assistant Examiner*—Gregory A. Morse
*Attorney, Agent, or Firm*—Mark C. Bach

[57] ABSTRACT

A mover for moving a container and a method of moving a container are provided. One container mover comprises a prime mover and a container engaging element operatively connected with the prime mover such that the container engaging element moves responsive to the prime mover to move the container. A driver is operatively connected with the container engaging element for moving the container engaging element between a first position where the container engaging element engages the container and a second position where the container engaging element is offset from the container. In one method of moving a container with a container mover including a container engaging element, the container engaging element is moved such that the container engaging element engages the container. The container engaging element and the container are moved conjointly. The container engaging element is moved such that the container engaging element is offset from the container.

20 Claims, 2 Drawing Sheets

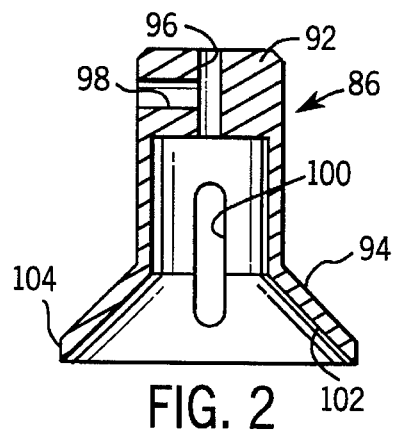
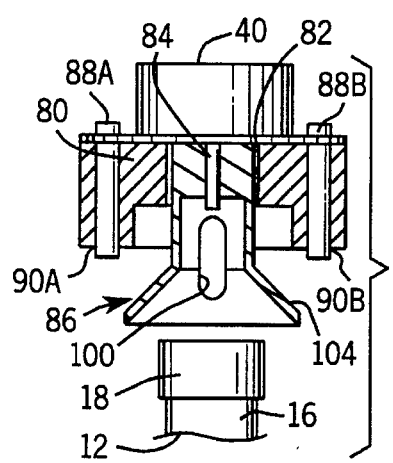
FIG. 2
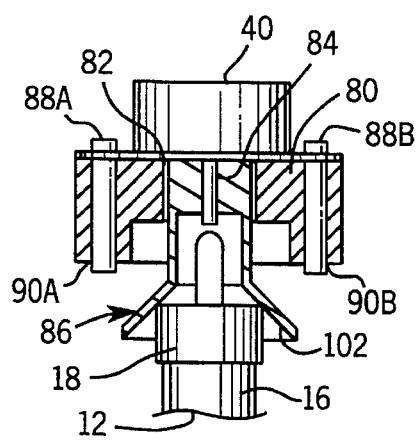
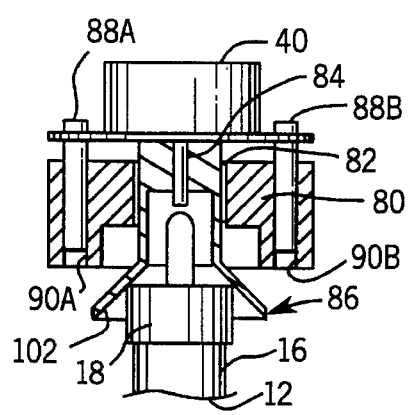
FIG. 3A
FIG. 3B  FIG. 3C
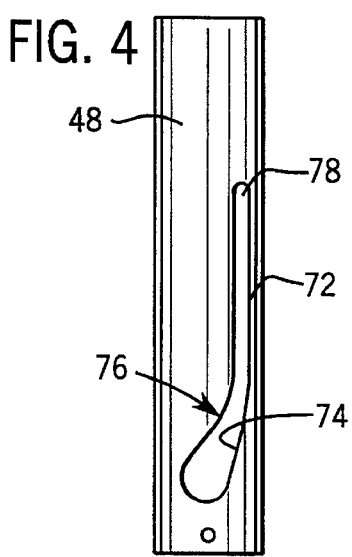
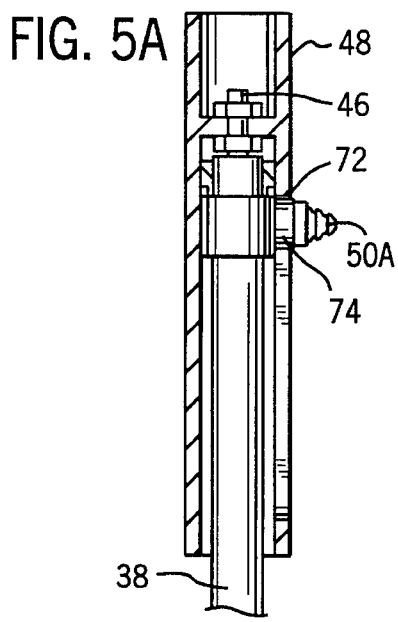
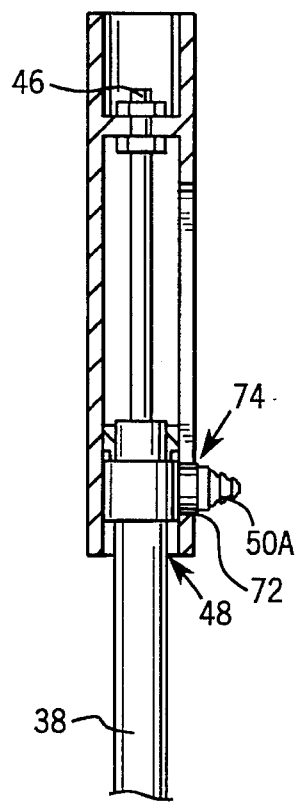
FIG. 4  FIG. 5A  FIG. 5B

CONTAINER MOVER AND METHOD OF MOVING A CONTAINER

BACKGROUND OF THE INVENTION

Embodiments described herein relate generally to moving a container automatically. More specifically, the embodiments relate to moving automatically a sample container in an automated analytical instrument, such as a blood analyzer and the like.

Analytical instruments are available for performing a number of functions. Some analytical instruments perform medical tests on biological samples, such as human blood and the like. These medical tests may determine if, for example, a certain patient's blood make-up shows that the patient suffers from a disease. To perform the medical tests, a number of things are done, such as counting cells, sorting cells and the like.

Because of the number of things done to the blood sample, the blood sample may be divided into separate portions, such as one portion for each of the things to be done with the blood. In order to remember from which patient the blood was taken, a name or identity code may be used and given to each of the separate portions. The separate portions of blood are processed during the medical tests performed by the analytical instrument. Information about the separate portions is gathered from the tests. Once all of the tests are complete, the information gathered from the tests about the blood sample is given to a medical professional. Because each of the separate portions of blood was given a name identifying the patient from whom the blood was taken, the medical professional can match the information to the proper patient.

However, in practice, matching the information gathered by the analytical instruments with a patient may not be easy. In some cases, many analytical instruments are used. These instruments may be located in different places. A container holding blood from the patient may be divided into portions in one place and the instruments may be in another place. During transport of the portions, the identity codes may be lost or become unreadable. Multiple identity codes may be used. All of these events can lead to mistakes in the information/patient matching process. Those mistakes may cause the wrong information to be matched with a patient. Thus, in an effort to reduce the probability of mistakes, it is desirable to name, to divide and to test the blood sample in the same place, preferably with the same instrument.

SUMMARY OF THE INVENTION

Embodiments described herein provide movers and methods for moving a container. In one embodiment, a container mover comprises a prime mover and a container engaging element operatively connected with the prime mover such that the container engaging element moves responsive to the prime mover to move the container. A driver is operatively connected with the container engaging element for moving the container engaging element between a first position where the container engaging element engages the container and a second position where the container engaging element is offset from the container.

According to another embodiment, a method of moving a container with a container mover including a container engaging element includes moving the container engaging element such that the container engaging element engages the container. The container engaging element and the container are moved conjointly. The container engaging element is moved such that the container engaging element is offset from the container.

BRIEF DESCRIPTION OF THE DRAWINGS

FIG. 2 is a sectional view of a container engaging element of the container mover of FIG. 1;

FIG. 3A is a partial sectional view of the container engaging element of FIG. 2 offset from a container;

FIG. 3B is a view similar to that of FIG. 3A showing the container engaging element engaging the container;

FIG. 3C is a view similar to that of FIG. 3B showing the container engaging element moving the container;

FIG. 4 is a side elevational view of an element of the construction of FIG. 1;

FIG. 5A is a partially sectioned view of the element of FIG. 4 associated with an elevator in a first position; and FIG. 5B is a view similar to that of FIG. 5A showing the element in a second position.

DETAILED DESCRIPTION OF PREFERRED EMBODIMENTS

Figure 1:
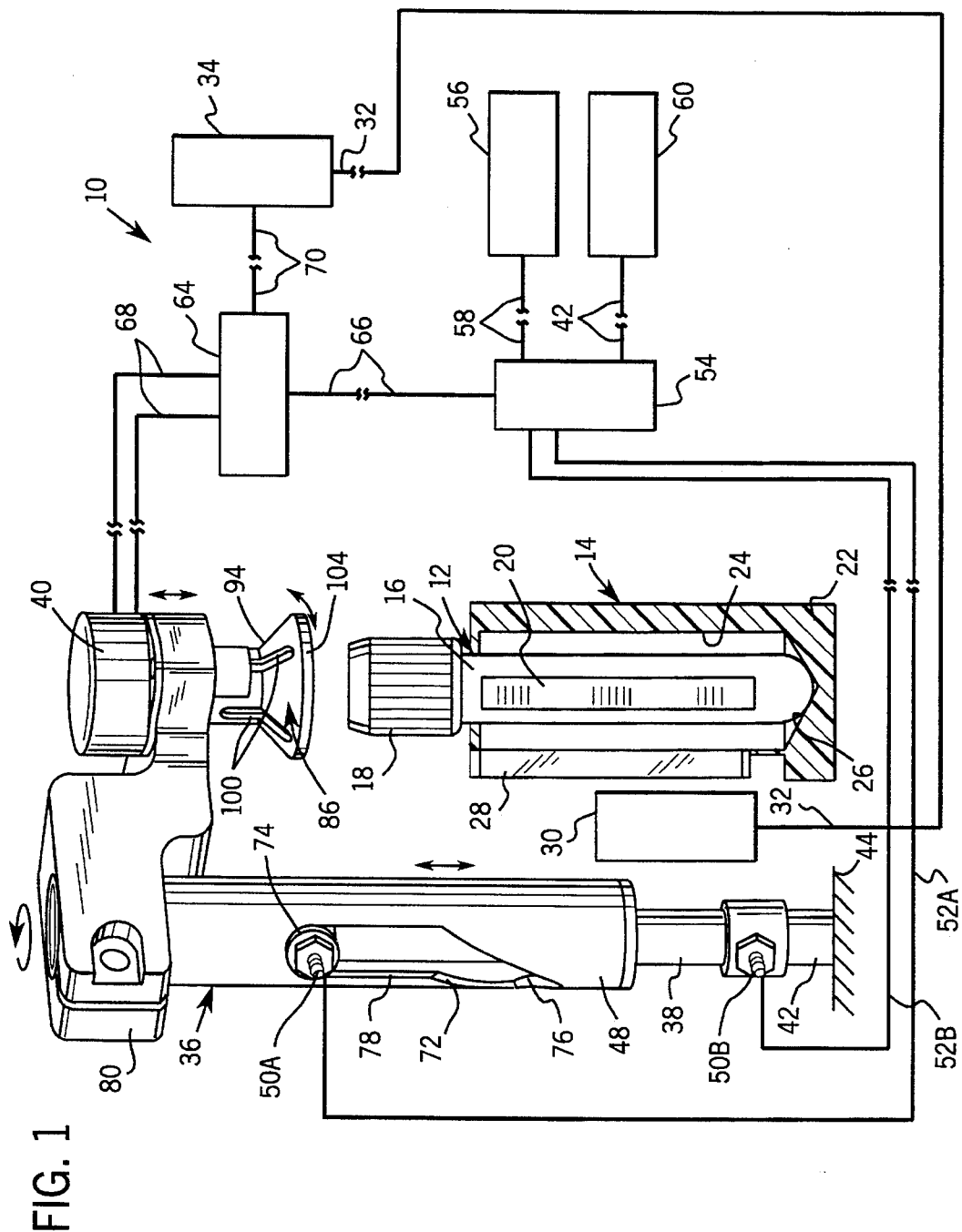
FIG. 1 illustrates an exemplary construction of a container mover with structural relationships exaggerated for clarity.

FIG. 1 illustrates a container mover 10 for moving a container 12. The container mover 10 may be used in a number of situations. However, for the sake of clarity, the container mover 10 will be discussed with respect to its employment with an automated analytical instrument, such as the instrument disclosed in U.S. patent application Ser. No. 08/283,379 filed on Aug. 1, 1994. That patent application is assigned to the assignee of the present case and the disclosure thereof, in its entirety, is incorporated herein by this reference. As will be pointed out in detail, the container mover 10 can be used to facilitate identification of a given container 12, facilitate processing of contents of the container 12, such as by maintaining suspension of particles in a fluid, resuspension of particles in fluid, etc. The container mover 10 is constructed such that it can function effectively with a plurality of different containers 12 having various external configurations, sometimes with appropriate dimensional adaptations and the like. It is to be remembered that elements of the constructions and method described herein may be arranged in any suitable fashion to arrive at yet further constructions and methods. For instance, the steps of one method may be arranged with steps of another method to arrive at yet another method.

Referring again to FIG. 1, the container mover 10 comprises a container holder 14 for accepting the container 12. The container 12 generally comprises a tubular member 16 and a cap 18. An identifier 20, such as a bar code and the like, can be disposed on the container 12 for facilitating identification of the container 12 and/or its contents. For example, the if the container 12 were a blood sample tube, then the identifier 20 may contain information about the patient from whom the blood sample was taken. This information is important so that results of tests performed on the blood sample can be linked to the proper patient.

The container holder 14 comprises a body 22 having at least one bore 24 dimensioned for accepting the container 12. The body 22 may include structures for allowing automated movement of the body 22 along a container 12 processing path associated with an automated analytical instrument. The body 22 may be formed from any suitable material. In an exemplary embodiment, the body 22 is composed of a suitable polymer, such as polyurethane and the like. The body 22 itself may include an identifier, such as a bar code and the like, to facilitate identification of a particular body 22. There may be a plurality, such as ten, of bores 24 on a single body 22. Each bore 24 is dimensioned and configured to accept and to support the container 12. In the illustrated embodiment, the bore 24 is substantially cylindrical and has a diameter of about 0.645 inches and a depth of about 1.75 inches. A closed end 26 of the bore 24 may be inclined to facilitate movement, i.e. rotation, of the container 12 within the bore 24. In the illustrated embodiment, the closed end 26 defines an angle of about 118 degrees.

Associated with the bore 24 is a window 28. The window 28 provides an access to the interior of the bore 24 from outside of the body 22. The window 28 is dimensioned for exposure of the identifier 20 on the container 12 to a sensor 30, such as a bar code reader and the like. The sensor 30 is operatively associated with or located with respect to the window 28 to sense or to read the identifier 20. In an exemplary embodiment, the window 28 is about 0.187 inches wide and about 1.5 inches long. In one embodiment, the sensor 30 is a fixed mount bar code scanner, such as number 25-NFT21-01 available from Opticon Inc. of Orangeburg, N.Y., and the like. The sensor 30 is electrically connected by conductor 32 with a computer 34, having memory, such as a RAM, a ROM, an EPROM, a SRAM and the like, containing appropriate routines, which controls the analytical instrument with which the container mover 10 is operatively associated.

A driver or driving apparatus 36 is disposed adjacent the container holder 14 such that the driving apparatus 36 is able to access the container 12 within the bore 24 in the body 22 of the container holder 14 to move the container 12. The driving apparatus 36 generally comprises an elevator 38 and a prime mover 40 operatively associated with the elevator 38. The elevator 38 moves the prime mover 40, as well as structures described below operatively associated with the prime mover 40, with respect to the container 12 in the container holder 14. In the illustrated embodiment, the elevator 38 is a fluidic or pneumatic cylinder, such as model 0072-DXP double acting, about 2 inch stroke length, stainless steel rod, available from Bimba Manufacturing Company of Monee, Ill.

A first end 42 of the elevator 38 is attached to a support surface 44. A second end or piston 46 of the elevator 38 is attached to a substantially cylindrical sleeve member 48 which substantially surrounds and is located coaxially with the second end 46 of the elevator 38, as shown in FIGS. 5A and 5B. The sleeve member 48 is operatively associated with the elevator 38 and a container engaging element, described below, such that the container engaging element moves between a first position and a second position responsive to operation of the elevator 38. As will become clear, the sleeve member 48 rotates about the elevator 38 as the opposite ends of the elevator 38 relatively move. The sleeve member 48 may be constructed from any suitable material. In an exemplary embodiment, the sleeve member 48 is made from a metal, such as stainless steel and the like. In the illustrated embodiment, the sleeve member 48 is about 4 inches long and has an outer diameter of about 0.75 inches and an inner diameter of about 0.68 inches.

The elevator 38, in the illustrated embodiment, has two ports 50A and 50B. The ports 50A and 50B are fluidly connected by conduits 52A and 52B, respectively, to a valve 54. The valve 54, in turn, is fluidly connected to a source 56 of relatively increased pressure by conduit 58 and to a source 60 of relatively reduced pressure by conduit 62. In an exemplary embodiment, the source 56 may be a pressure pump and the source 60 may be a vent to atmospheric or ambient pressure. A pressure differential between the sources 56 and 60 induces action of the elevator 38. In an exemplary embodiment, the valve 54 is a 4 way, 2 position, single solenoid valve, such as number NV J3143-5LZ available from SMC Pneumatics Inc. of Indianapolis, Ind.

The valve 54 is electrically connected with a controller 64 by conductor 66. In this way, the controller 64 can send an electrical signal to the valve 54 thereby determining which port 50A or 50B is fluidly connected with which source 56 or 60. The controller 64 is also electrically connected with the prime mover 40 by conductor 68 and with computer 34 by conductor 70. In this way, as will be discussed in greater detail later, operation of elements of the container mover 10 can be coordinated and monitored.

Action of the elevator 38 is determined by which source 56 or 60 is fluidly connected to which port 50A or 50B by the valve 54. If the source 56 were fluidly connected with the port 50B and the source 60 were fluidly connected with the port 50A, then the second end 46 of the elevator 38 would move away from the first end 42 of the elevator 38. Alternatively, if the source 56 were fluidly connected with the port 50A and the source 60 were fluidly connected with the port 50B, then the second end 46 of the elevator would move towards the first end 42 of the elevator 38. Because the prime mover 40 is operatively connected with the elevator 38, movement of the second end 48 with respect to the first end 42 causes corresponding movement of the prime mover 40 with respect to the container 12 in the container holder 14. For instance, as illustrated, movement of the second end 48 away from the first end 42 causes the prime mover 40 to move away from the container 12 in the container holder 14. This can facilitate placement of the container 12 in and removal of the container 12 from the bore 24 in the body 22 of the container holder 14.

In some embodiments, it may be desirable to move the prime mover 40 with respect to the container 12 in the container holder 14 through more than one direction. To do this, as shown in FIGS. 1, 4, 5A and 5B, a slot 72 is operatively associated with or provided in the sleeve member 48. This slot 72 cooperates with a cam surface 74 operatively associated with the port 50A responsive to movement of the second end 46 with respect to the first end 42. The slot 72 is specifically configured to provide the desired motion of the prime mover 40 with respect to the container 12.

Illustrating by example, the slot 72 is about 0.377 inches wide and the length of the slot 72 axially along the sleeve member 48 is about 2 inches. A portion 76 of the slot 72 closest to the first end 42 defines a circumferential incline along relevant sections of the circumference of the sleeve member 48. The portion 76 is about 0.75 inches long. An end of the portion 76 proximate to the second end 46 is connected with another portion 78 of the slot 72. The portion 78 extends about 1.25 inches along the sleeve member 48 substantially parallel to an axis of elongation of the sleeve member 48. This configuration of the slot 72 causes rotation of the sleeve member 48, and any structures operatively attached thereto, through an angle, of about 60 degrees in an exemplary embodiment, responsive to movement of the second end 46 between a first position illustrated in FIG. 5B and a second position illustrated in FIGS. 1 and 5A.

The prime mover 40 is operatively connected with the sleeve member 48 by an arm 80. The arm 80 is fixed with respect to the sleeve member 48 such that the arm 80, and therefore the prime mover 40, moves correspondingly with the sleeve member 48. The arm 80 may be made from any suitable material. In an exemplary embodiment, the arm 80 is made from a polymer, such as polyurethane and the like.

In an exemplary embodiment, the prime mover 40 is an electric motor which moves the container 12 within the bore 24 in the body 22 such that the identifier 20 on the tubular member 16 is exposed through the window 28 to the sensor 30 sufficiently such that the sensor 30 can "read" the identifier 20. In a particular embodiment, the prime mover 40 is a stepper motor, such as a Series N82100 stepper motor, available from Phillips Technologies Airpax Mechatronics Group of Cheshire, Conn., and the like. During operation of this exemplary embodiment, the stepper motor runs at a rate of about 200 steps per second, which is equivalent to about 250 rpm's.

As shown in FIGS. 3A, 3B and 3C, the arm 80 includes an aperture 82 at one end for accepting a drive shaft 84 of the prime mover 40 and a container engaging element 86. The prime mover 40 is positioned with respect to the aperture 82 such that the drive shaft 84 extends into the aperture 82. The prime mover 40 includes, in the illustrated embodiment, two bearings 88A and 88B which are spaced from and extend parallel to the drive shaft 84. The arm 80 also includes bores 90A and 90B which accept the bearings 88A and 88B, respectively. Cooperation among the bearings 88A and 88B and the bores 90A and 90B allow the prime mover 40 to "float" or move, as shown sequentially in FIGS. 3A, 3B and 3C, with respect to the arm 80 along an axis of the aperture 82. The significance of this movement is discussed later.

Construction of the container engaging element 86 is illustrated in detail in FIG. 2. The container engaging element 86 is configured to facilitate force (i.e. torque) transfer from the drive shaft 84 of the prime mover 40 to the container 12 being moved by the container mover 10. Because it is desirable that the container mover 10 be useable with a number of different containers 12 having different external configurations, the container engaging element 86 includes structures complementary to the appropriate configurations of the containers 12.

In the embodiment shown in FIG. 2, the container engaging element 86 generally comprises a substantially cylindrical body 92 and a substantially frusto-conical portion 94 depending from the body 92. To operatively connect the body 92 and the prime mover 40, the body 92 includes a bore 96 for accepting the drive shaft 84 of the prime mover 40. To provide conjoint rotation of the container engaging element 86 and the drive shaft 84, another bore 98 is provided in the body 92 of the container engaging element 86. The bore 98 is disposed substantially orthogonally to the bore 96 such that the bore 98 can accept a fastener, not shown, such as a set screw and the like, which threadibly engages the body 92 and bears against the drive shaft 84.

When the drive shaft 84 is located within the bore 96 and the fastener is applied, dimensional tolerances present within the prime mover 40, arm 80 and container engaging element 86 system allow for movement of the prime mover 40, conjointly with the container engaging element 86, along an axis defined by the aperture 82. In an exemplary embodiment, the magnitude of this movement is about 0.65 inches. This movement allows the container mover 10 to accommodate containers 12 of various lengths. Also, this movement limits the axial force applied to the container 12 by the container mover 10. The axial force applied to the container 12 by the container mover 10 corresponds to weight of the prime mover 40 and the container engaging element 86. Forces generated by the elevator 38 are not applied to the container 12, which might break under such forces.

The frusto-conical portion 94 is constructed to substantially center or align the container 12 with the container engaging element 86 as the container engaging element 86 moves with respect to the container 12. Centering may be of interest especially if the container 12 has an outer diameter significantly smaller than the diameter of the bore 24 in the body 22. The configuration of the portion 94 compensates for variance in outer diameters of the caps 18 of the various containers 12 to be used with the container mover 10. The frusto-conical configuration of the portion 94 can also reduce the likelihood that the element 86 might come into contact with container 12 contents on the cap 18. The portion 94 also increases torque transmission from the drive shaft 84 of the prime mover 40 to the container 12 by allowing for contact between a container engaging surface 102 on the element 86 and a relatively large radius surface of the cap 18.

At least one slot 100 is provided on the container engaging element 86. The slot 100 facilitates torque transfer from the container engaging element 86 to the container 12 by providing an increased frictional grip on the container 12, specifically the cap 18. Friction between the element 86 and the cap 18 should not be substantially reduced, even if the cap 18 were coated with a fluid, such as water, blood and the like. The frictional grip can be increased further if the cap 18 were to have certain structure, such as an external knurl and the like. The slot 100 extends from the interior, container engaging surface 102 of the container engaging element 86 to an outer surface 104 of the element 86. Thus, the slot 100 can increase container 12 compatibility of the container mover 10. For instance, some containers 12 manufactured by Sarstedt include caps 18 having relatively small outer diameter surfaces, thereby reducing efficiency of torque transfer from the drive shaft 84 to the container 12. However, these containers 12 include a key of sorts to facilitate processing. The key can be located within the slot 100 to facilitate torque transfer.

In an exemplary embodiment, the container engaging element 86 is made from a suitable material, such as anodized aluminum and the like. The element 86 is about 1.104 inches in axial length with the frusto-conical portion 94 being about 0.335 inches in axial length. A maximum diameter defined by the body 92 is about 0.5 inches and by the container engaging surface 102 of the element 86 is about 1 inch. The container engaging surface 102 of the frusto-conical portion 94 defines an angle of about 90 degrees. There are four slots 100 spaced substantially equidistantly on the element 86. Each slot 100 is about 0.5 inches in axial length and about 0.13 inches in width.

With the construction of the container mover 10 being thusly described in detail, methods of operation of the mover 10, and methods for moving a container 12 in general, will be discussed. It is to be noted that, for the sake of clarity, an exemplary method will be discussed in detail. However, other methods are also possible.

It is assumed that the container mover 10 begins in a "rest" position. The elevator 38 and the sleeve member 48 are in the position illustrated in FIG. 5B, viz. the cam surface 74 is disposed at a terminal end of the portion 76 of the slot 72 opposite to the end of the portion 76 adjacent the portion 78 of the slot 72. In this position, the container engaging element 86 is rotated about 60 degrees away from an axis of elongation of the bore 24 in the body 22 of the container holder 14 shown in FIG. 1. With the container mover 10 in this position, an operator can place a container 12 in the bore 24 in the container holder 14. Alternatively, a container holder 14 bearing containers 12 may be appropriately positioned with respect to the container mover 10 such that the containers 12 therein are accessible to the container mover 10. The valve 54 is in a first position where the source 56 of relatively increased pressure is fluidly coupled with the port 50B through conduit 52B and the source 60 of relatively reduced pressure is fluidly connected with port 50A through conduit 52A.

The operator places a container 12 in the bore 24 in the container holder 14 and causes the computer 34 to send an electrical signal to the controller 64 through conductor 70. The controller 64 sends an electrical signal to valve 54 through conductor 66. The valve 54 indexes such that the source 56 of relatively increased pressure is fluidly connected with the port 50A through conduit 52A and the source 60 of relatively reduced pressure is fluidly connected to the port 50B through conduit 52B. Because of the pressure differential between the sources 56 and 60, the elevator 38 is activated such that the second end 46 of the elevator 38 approaches the first end 42 of the elevator 38. The elevator 38 and the sleeve member 48 approach the position illustrated in FIG. 5A. As the elevator 38 and the sleeve member 48 approach the position of FIG. 5A, the container engaging element 86 is moved through an angle, of about 60 degrees in this exemplary embodiment, towards the axis of elongation of the bore 24 in the body 22 on the container holder 14. This rotation is performed under the influence of the cam surface 74 camming along the inclined portion 76 of the slot 72 responsive to movement of the second end 46 of the elevator 38 with respect to the first end 42 of the elevator 38.

As the cam surface 74 reaches a juncture between the portion 76 and the portion 78 of the slot 72, rotation of the arm 80, and thereby the container engaging element 86 ceases. However, movement of the container engaging element 86 continues. Referring to FIGS. 3A, 3B and 3C, as the elevator 38 and the sleeve member 48 approach the position illustrated in FIG. 5A, the container contacting surface 102 of the container engaging element 86 approaches the cap 18 on the container 12. The container engaging element 86 is offset from the cap 18 of the container 12 by a certain distance as the cam surface 74 enters the portion 78 of the slot 78. This distance is represented in FIG. 3A. In this method, the container engaging element 86 is first rotated towards an axis of the bore 24 and then moved along the axis of the bore 24 towards the cap 18 on the container 12.

As shown in FIG. 3B, the second end 46 of the elevator 38 continues to move toward the first end 42 of the elevator 38 as the cam surface 74 cams along the portion 78 of the slot 72. When the cam surface 74 has cammed a certain distance along the slot 72, the container engaging surface 102 of the container engaging element 86 contacts the surface of the cap 18 on the container 12. The incline of the container engaging surface 102 given by the frusto-conical portion 94 of the container engaging element 86 directs the cap 18 and thereby the container 12. The direction offered by the container engaging surface 102 causes the container 12 to become centered on and aligned with the container engaging element 86.

As FIGS. 1 and 5A show, the cam surface 74 reaches a terminal end of the portion 78 of the slot 72. A range of movement of the cam surface 74 within the slot 72 can be limited in a number of ways, such as by interference between the cam surface 74 and terminal ends of the slot 72, appropriately choosing the elevator 38 such that its stroke is limited, etc.

The prime mover 40 moves with respect to the arm 80 such that the only axial force applied to the cap 18 and the container 12 corresponds to the combined weight of the prime mover 40 and the container engaging portion 86. In one embodiment, this weight is about an ounce or two. This movement is facilitated by sliding of the bearings 88A and 88B, which are fixed to the prime mover 40, within bores 90A and 90B, respectively. In this manner, unnecessarily large axial forces are not applied to the container 12. If a sufficiently large axial force were applied to the container 12, the container 12 might break, rotation of the container 12 within the bore 24 conjointly with the prime mover 40 and the container engaging element 86 might be limited, etc.

At any time during the above-described steps, the controller 64 can send an electrical signal to the prime mover 40 to initiate operation of the prime mover 40. In this manner, the container engaging element 86 can contact the cap 18 of the container 12 while the element 86 is substantially rotatably stationary with respect to the container 12 or while the element 86 is rotating with respect to the container 12. In either case, the prime mover 40 rotates the container 12 for a specific, predetermined time period. This time period is sufficient to permit the sensor 30 to read the identifier 20 on he container 12 many times and to verify that successive readings of the identifier 20 are identical. In an exemplary embodiment, this time period is about 12 seconds. The information read from the identifier 20 may be passed by the sensor 30 to the computer 34 along conductor 32. The time period may also be sufficient to provide for other desired items, such as maintaining particle suspension in a fluid disposed within the container 12, resuspending particles etc.

once the predetermined time period has expired, the controller 64 ceases operation of the prime mover 40. The container 12 comes to rest within the bore 24 in the body 22 of the container holder 14. At this point, the controller 64 issues electrical signals to the valve 54 such that the above-described process of moving the container engaging element 86 with respect to an axis of the bore 24 is reversed. Namely, the container engaging element 86 is moved axially away from the container 12 and then the element 86 is rotated through an angle, about 60 degrees in an exemplary embodiment, away from the axis of the bore 24. The container 12 and its contents are ready for further processing, which may take place while the container 12 is in the bore 24 in the container holder 14 or at a separate location. If further processing, such as removal of container 12 contents and the like, were to take place at the same location, then the likelihood that the contents of the container 12, either before or after subsequent processing, would be improperly identified could be reduced.

What is claimed is:

1. A mover for moving a container comprising:

(a) a prime mover;

(b) a container engaging element operatively connected with the prime mover such that the container engaging element moves responsive to the prime mover to move the container, the container engaging element substantially surrounding a portion of the container when the container engaging element is moving the container, wherein the container engaging element has a fixed lower surface which contacts the container when the container engaging element is moving the container, the lower surface having a first portion dimensioned to engage a container of a first size and a second portion, disposed above the first portion, dimensioned to engage a container of a second size; and (c) a driver operatively connected with the container engaging element for moving the container engaging element between a first position where the container engaging element engages the container and a second position where the container engaging element is offset from the container.

2. A mover as defined in claim 1 further comprising:

(d) a container holder operatively associated with the container engaging element for supporting the container.

3. A mover as defined in claim 2 wherein the container holder includes a window for exposing the container supported by the container holder.

4. A mover as defined in claim 3 further comprising:

(e) a sensor operatively associated with the window such that the sensor senses the container supported by the container holder.

5. A mover as defined in claim 4 further comprising an identifier disposed on the container sensible by the sensor.

6. A mover as defined in claim 1 wherein the driver comprises:

(i) an elevator; and (ii) a sleeve member operatively associated with the elevator and the container engaging element such that the container engaging element moves between the first position and the second position responsive to operation of the elevator.

7. A mover as defined in claim 6 wherein the elevator comprises a fluidic cylinder.

8. A mover as defined in claim 1 further comprising:

(d) an arm operatively connecting the prime mover with the driver such that the prime mover moves responsive to operation of the driver.

9. A mover as defined in claim 8 further comprising:

(i) a bearing operatively associated with the prime mover; and (ii) a bore operatively associated with the arm, the bearing being slidably engagable with the bore such that the prime mover can move with respect to the arm.

10. A mover as defined in claim 1 wherein the prime mover is an electric motor.

11. A mover as defined in claim 1 wherein the container engaging element is made of a metal.

12. A mover as defined in claim 1 wherein the container engaging element includes (i) a slot to facilitate force transfer from the prime mover to the container.

13. A mover for moving a container comprising:

(a) prime mover;

(b) a container engaging element operatively connected with the prime mover such that the container engaging element moves responsive to the prime mover to move the container, the container engaging element substantially surrounding a portion of the container when the container engaging element is moving the container, the container engaging element comprising;

(i) a body operatively connectable with the prime mover; and (ii) a frusto-conical portion engagable with the container to facilitate force transfer from the prime mover to the container and (c) a driver operatively connected with the container engaging element for moving he container engaging element between a first position where the container engaging element engages the container and a second position where the container engaging element is offset from the container.

14. A mover for moving a container comprising;

(a) a prime mover;

(b) a container engaging element operatively connected with the prime mover such that the container engaging element moves responsive to the prime mover to move the container;

(c) a driver operatively connected with the container engaging element for moving the container engaging element between a first position where the container engaging element engages the container and a second position where the container engaging element is offset from the container, the driver including (i) an elevator; and (ii) a sleeve member operatively associated with the elevator and the container engaging element such that the container engaging element moves between the first position and the second position responsive to operation of the elevator;

(d) a cam operatively associated with the elevator; and (e) a slot operatively associated with the sleeve member, the cam camming along the slot responsive to operation of the elevator.

15. A mover as defined in claim 14 wherein the slot includes a first portion and a second portion, the first portion defining an incline on the sleeve member and the second portion extending substantially parallel to an axis of the sleeve member.

16. A method of moving a container with a container mover including a container engaging element, the method comprising the steps of:

(a) moving the container engaging element such that the container engaging element substantially surrounds the container when the container engaging element is moving the container, wherein the container engaging element has a fixed lower surface which contacts the container when the container engaging element is moving the container, the lower surface having a first portion dimensioned to engage a container of a first size and a second portion, disposed above the first portion, dimensioned to engage a container of a second size;

(b) moving the container engaging element and the container conjointly; and (c) moving the container engaging element such that the container engaging element is offset from the container.

17. A method as defined in claim 16 wherein the moving step (a) includes:

(i) first, moving the container engaging element toward an axis of the container; and (ii) second, moving the container engaging element substantially along the axis of the container.

18. A method as defined in claim 16 wherein the moving step (b) includes:

(i) rotating the container and the container engaging element substantially about an axis of the container.

19. A method as defined in claim 16 wherein the moving step (c) includes:

(i) first, moving the container engaging element substantially along an axis of the container, and (ii) second, moving the container engaging element away from the axis of the container.

20. A method as defined in claim 16 further comprising the step of:

(d) sensing an identifier on the container.

* * * * *

UNITED STATES PATENT AND TRADEMARK OFFICE
CERTIFICATE OF CORRECTION

PATENT NO. : 5,551,828
DATED : September 3, 1996
INVENTOR(S) : Kenneth E. Iles

It is certified that error appears in the above-indentified patent and that said Letters Patent is hereby corrected as shown below:

Column 10, line 3, change ";" to --:--.

Signed and Sealed this

Eleventh Day of March, 1997

Attest:

BRUCE LEHMAN

*Attesting Officer*   Commissioner of Patents and Trademarks